United States Patent
Kanda

(10) Patent No.: US 10,765,297 B2
(45) Date of Patent: Sep. 8, 2020

(54) IMAGE PROCESSING APPARATUS, IMAGE PROCESSING METHOD, AND COMPUTER READABLE RECORDING MEDIUM

(71) Applicant: OLYMPUS CORPORATION, Tokyo (JP)

(72) Inventor: Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 120 days.

(21) Appl. No.: 16/015,346

(22) Filed: Jun. 22, 2018

(65) Prior Publication Data

US 2018/0317744 A1 Nov. 8, 2018

Related U.S. Application Data

(63) Continuation of application No. PCT/JP2015/086425, filed on Dec. 25, 2015.

(51) Int. Cl.
*G06T 7/00* (2017.01)
*A61B 1/00* (2006.01)
(Continued)

(52) U.S. Cl.
CPC ........ *A61B 1/00009* (2013.01); *A61B 5/0022* (2013.01); *A61B 5/1072* (2013.01); *G06K 9/209* (2013.01); *G06K 9/6255* (2013.01); *G06K 9/6256* (2013.01); *G06T 7/0014* (2013.01); *G06T 7/529* (2017.01); *G06T 11/003* (2013.01); *A61B 5/7264* (2013.01); *G06K 2209/05* (2013.01); *G06T 2207/10024* (2013.01); *G06T 2207/10068* (2013.01);
(Continued)

(58) Field of Classification Search
None
See application file for complete search history.

(56) References Cited

U.S. PATENT DOCUMENTS 8,903,167 B2 12/2014 Kohli et al.
2009/0161927 A1* 6/2009 Mori ............... A61B 6/466
382/128
(Continued)

FOREIGN PATENT DOCUMENTS

EP 2 548 495 A1 1/2013
EP 2548495 A1 * 1/2013 ............ A61B 5/064
(Continued)

OTHER PUBLICATIONS

International Search Report dated Mar. 29, 2016 issued in PCT/JP2015/086425.
(Continued)

*Primary Examiner* — Delomia L Gilliard
(74) *Attorney, Agent, or Firm* — Scully, Scott, Murphy & Presser, P.C.

(57) ABSTRACT

An image processing apparatus includes: a surface shape estimation unit configured to estimate a surface shape of a target that appears in an intraluminal image of a living body; an imaging viewpoint changing unit configured to change an imaging viewpoint with respect to the surface shape from an imaging viewpoint used for estimation; and an image generation unit configured to generate a virtual image of the target for a case of imaging the target from the changed imaging viewpoint.

21 Claims, 11 Drawing Sheets

(51) Int. Cl.
*A61B 5/107* (2006.01)
*A61B 5/00* (2006.01)
*G06T 7/529* (2017.01)
*G06K 9/20* (2006.01)
*G06K 9/62* (2006.01)
*G06T 11/00* (2006.01)
*H04N 5/232* (2006.01)
*H04N 5/225* (2006.01)

(52) U.S. Cl.
CPC .............. *G06T 2207/20081* (2013.01); *G06T 2207/30028* (2013.01); *G06T 2210/41* (2013.01); *H04N 5/23229* (2013.01); *H04N 2005/2255* (2013.01)

(56) References Cited

U.S. PATENT DOCUMENTS

2012/0288186 A1  11/2012  Kohli et al.
2012/0316421 A1*  12/2012  Kumar ............... A61B 1/00009
                                                                600/407
2015/0272423 A1  10/2015  Ito et al.
2015/0279111 A1*  10/2015  Sugiura ................ G06T 7/0012
                                                                345/424

FOREIGN PATENT DOCUMENTS

EP        2 918 218 A1      9/2015
EP        2918218 A1  *     9/2015  ............... A61B 6/12
JP        2011-036600 A     2/2011
JP        2011-172692 A     9/2011
JP        2011172692 A  *   9/2011
JP        5715312 B2         5/2015

OTHER PUBLICATIONS

Extended Supplementary European Search Report dated Aug. 1, 2019 in European Patent Application No. 15 91 1431.3.

* cited by examiner

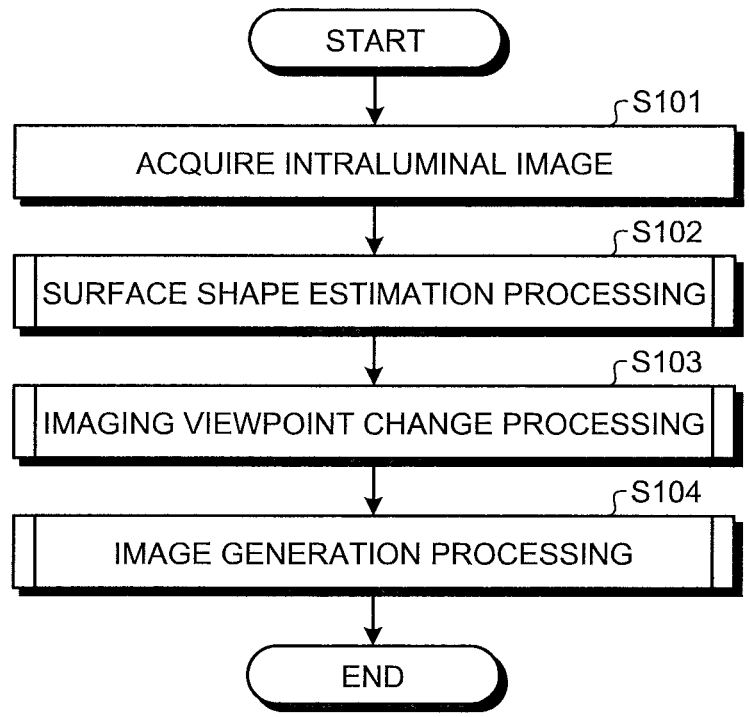

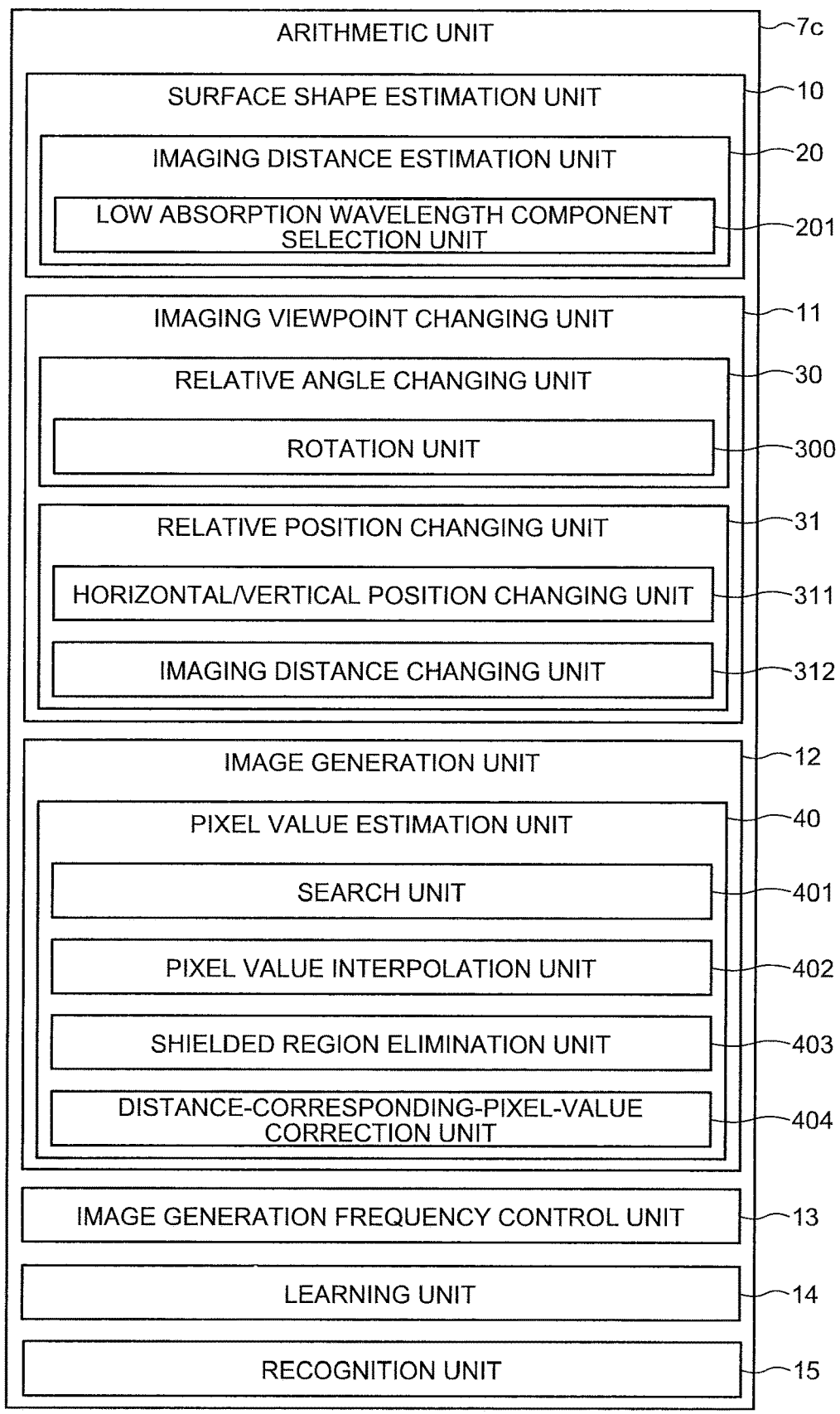

IMAGE PROCESSING APPARATUS, IMAGE PROCESSING METHOD, AND COMPUTER READABLE RECORDING MEDIUM

CROSS-REFERENCE TO RELATED APPLICATION

This application is a continuation of PCT International Application No. PCT/JP2015/086425 filed on Dec. 25, 2015, the entire contents of which are incorporated herein by reference.

BACKGROUND

The present disclosure relates to an image processing apparatus, an image processing method, and a computer readable recording medium.

In the related art, a technique for recognizing a specific region, such as an abnormal region, using a recognition criterion in an intraluminal image that is obtained by imaging inside a lumen (inside a gastrointestinal tract) of a living body by using a medical observation apparatus, such as an endoscope, has been known. The recognition criterion used in this technique is usually generated based on a wide range of variations of images of a normal mucosal region or an abnormal region that are extracted as learning samples from intraluminal images.

As a technique related to image recognition, for example, U.S. Pat. No. 8,903,167 discloses a technique for generating a new image by performing processing of changing a position, a size, and an orientation of any region of interest in an image acquired as a learning sample, and a technique for generating a recognition criterion by calculating a feature amount from the new image and an original image.

SUMMARY

An image processing apparatus according to one aspect of the present disclosure includes: a surface shape estimation unit configured to estimate a surface shape of a target that appears in an intraluminal image of a living body; an imaging viewpoint changing unit configured to change an imaging viewpoint with respect to the surface shape from an imaging viewpoint used for estimation; and an image generation unit configured to generate a virtual image of the target for a case of imaging the target from the changed imaging viewpoint.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a flowchart illustrating an outline of processing performed by the image processing apparatus according to the first embodiment;

FIG. 3 is a diagram illustrating an example of an intraluminal image;

FIG. 16 is a block diagram illustrating a configuration of an arithmetic unit according to a third embodiment.

DETAILED DESCRIPTION

Embodiments of an image processing apparatus, an image processing method, and a program according to the present disclosure will be described below with reference to the drawings. The present disclosure is not limited by the embodiments below. Further, the same components are denoted by the same reference signs throughout the drawings.

First Embodiment

Configuration of Image Processing Apparatus

Figure 1:
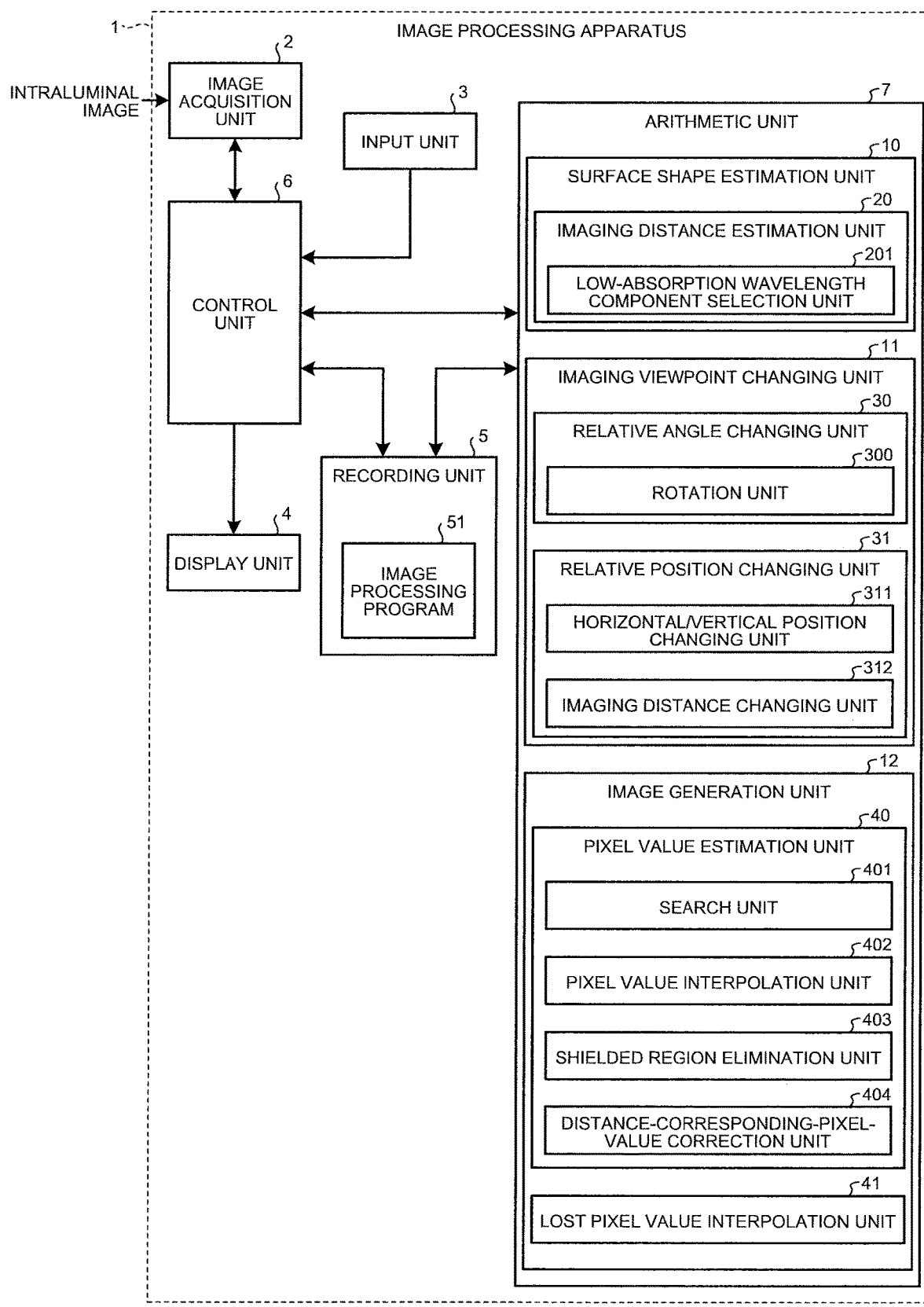
FIG. 1 is a block diagram illustrating a configuration of an image processing apparatus according to a first embodiment.

FIG. 1 is a block diagram illustrating a configuration of an image processing apparatus according to a first embodiment. An image processing apparatus 1 according to the first embodiment is, as one example, an apparatus that performs image processing of generating a new image (virtual image) with a different imaging viewpoint from an original intraluminal image, based on a surface shape of a target that appears in the intraluminal image that is acquired by imaging a lumen of a living body by an endoscope (an endoscopy scope, such as a flexible endoscope or a rigid endoscope) or a capsule endoscope (hereinafter, these are collectively and simply referred to as an "endoscope"). The intraluminal image is usually a color image with pixel levels (pixel values) corresponding to wavelength components of red (R), green (G), and blue (B) at each of pixel positions.

The image processing apparatus 1 illustrated in FIG. 1 includes an image acquisition unit 2 that acquires, from an endoscope or from outside, image data corresponding to an intraluminal image captured by the endoscope, an input unit 3 that receives an input signal that is input through external operation, a display unit 4 that displays the intraluminal image and various kinds of information, a recording unit 5 that records the image data acquired by the image acquisition unit 2 and various programs, a control unit 6 that controls the whole operation of the image processing apparatus 1, and an arithmetic unit 7 that performs predetermined image processing on the image data.

The image acquisition unit 2 is appropriately configured in accordance with a mode of a system including the endoscope. For example, when a portable recording medium is used for transmission and reception of image data to and from the endoscope, the image acquisition unit 2 is configured as a reader device to which the recording medium is detachably attachable and which may read the recorded image data. Further, when a server for recording the image data captured by the endoscope is used, the image acquisition unit 2 is configured with a communication device or the like capable of performing bi-directional communication with the server, and acquires the image data by performing data communication with the server. Furthermore, the image acquisition unit 2 may be configured with an interface device or the like to which the image data is input from the endoscope via a cable.

The input unit 3 is realized by, for example, an input device, such as a keyboard, a mouse, a touch panel, or various switches, and outputs the input signal that has been received in accordance with external operation to the control unit 6.

The display unit 4 is realized by a display device, such as a liquid crystal display panel or an organic electro luminescence (EL) display panel, and displays various screens including the intraluminal image under the control of the control unit 6.

The recording unit 5 is realized by any kind of integrated circuit (IC) memory, such as a flash memory, a read only memory (ROM), and a random access memory (RAM), and an internal hard disk, a hard disk connected via a data communication terminal, or the like. The recording unit 5 records a program for operating the image processing apparatus 1 and causing the image processing apparatus 1 to implement various functions, data used during execution of the program, and the like, in addition to the image data acquired by the image acquisition unit 2. For example, the recording unit 5 records an image processing program 51 for generating a new virtual image (learning sample) with a different imaging viewpoint from the intraluminal image, various kinds of information used during execution of the program, and the like.

The control unit 6 is realized by a central processing unit (CPU) or the like, and configured to read various programs recorded in the recording unit 5 and comprehensively control the whole operation of the image processing apparatus 1 by transferring an instruction, data, and the like to each of the units of the image processing apparatus 1 in accordance with the image data input from the image acquisition unit 2, the input signal input from the input unit 3, or the like.

The arithmetic unit 7 is realized by a CPU or the like, and configured to read the image processing program 51 recorded in the recording unit 5 and perform image processing of generating a virtual image with a different imaging viewpoint with respect to a target that appears in the intraluminal image.

Detailed Configuration of Calculation Unit

Next, a detailed configuration of the arithmetic unit 7 will be described.

The arithmetic unit 7 includes a surface shape estimation unit 10, an imaging viewpoint changing unit 11, and an image generation unit 12.

The surface shape estimation unit 10 estimates a surface shape of a target that appears in an intraluminal image of a living body. The surface shape estimation unit 10 includes an imaging distance estimation unit 20.

The imaging distance estimation unit 20 estimates an imaging distance to the target that appears at each of pixels of the intraluminal image. The imaging distance estimation unit 20 includes a low absorption wavelength component selection unit 201.

The low absorption wavelength component selection unit 201 selects a low absorption wavelength component, for which a degree of absorption and dispersion inside a living body is low, in the intraluminal image.

The imaging viewpoint changing unit 11 changes an imaging viewpoint with respect to the surface shape estimated by the surface shape estimation unit 10. The imaging viewpoint changing unit 11 includes a relative angle changing unit 30 and a relative position changing unit 31.

The relative angle changing unit 30 changes a relative angle between the surface shape estimated by the surface shape estimation unit 10 and the imaging viewpoint. The relative angle changing unit 30 includes a rotation unit 300 that rotates any of roll, yaw, and pitch with respect to the imaging direction of the endoscope.

The relative position changing unit 31 changes relative positions of the surface shape estimated by the surface shape estimation unit 10 and the imaging viewpoint. The relative position changing unit 31 includes a horizontal/vertical position changing unit 311 that changes horizontal positions and/or vertical positions of the surface shape and the imaging viewpoint, and an imaging distance changing unit 312 that changes an imaging distance from the surface shape to the imaging viewpoint.

The image generation unit 12 generates a virtual image of the target for a case of imaging the target from the changed imaging viewpoint. The image generation unit 12 includes a pixel value estimation unit 40 that estimates a pixel value of each of pixels of the virtual image based on pixel values of pixels of an intraluminal image that is projected on the virtual image due to a change in the imaging viewpoint, and a lost pixel value interpolation unit 41 that, when a pixel value of any of the pixels of the virtual image is lost, interpolates the pixel value of the subject pixel from pixels around the pixel whose pixel value is lost.

The pixel value estimation unit 40 includes a search unit 401 that searches for pixels of the intraluminal image that are projected around each of the pixels of the virtual image due to a change in the imaging viewpoint, a pixel value interpolation unit 402 that interpolates the pixel value of each of the pixels of the virtual image based on pixel values of the pixels of the intraluminal image obtained by search by the search unit 401, a shielded region elimination unit 403 that eliminates a pixel corresponding to a shielded region in the virtual image among the pixels of the intraluminal image projected on the virtual image, and a distance-corresponding-pixel-value correction unit 404 that corrects the pixel value of each of the pixels of the virtual image based on the imaging distance from the surface shape to the imaging viewpoint.

Processing Performed by Image Processing Apparatus

An image processing method performed by the image processing apparatus 1 configured as above will be described below. FIG. 2 is a flowchart illustrating an outline of processing performed by the image processing apparatus 1.

As illustrated in FIG. 2, first, the image processing apparatus 1 acquires an intraluminal image corresponding to image data, which is captured by the endoscope or the like, from outside via the image acquisition unit 2, and records the acquired intraluminal image in the recording unit 5 (Step S101). FIG. 3 illustrates an example of an intraluminal image W1 captured by the endoscope or the like from outside via the image acquisition unit 2.

Subsequently, the surface shape estimation unit 10 acquires the image data of the intraluminal image recorded in the recording unit 5, and performs surface shape estimation processing of estimating a surface shape of a target that appears in the acquired intraluminal image (Step S102).

Figure 4:
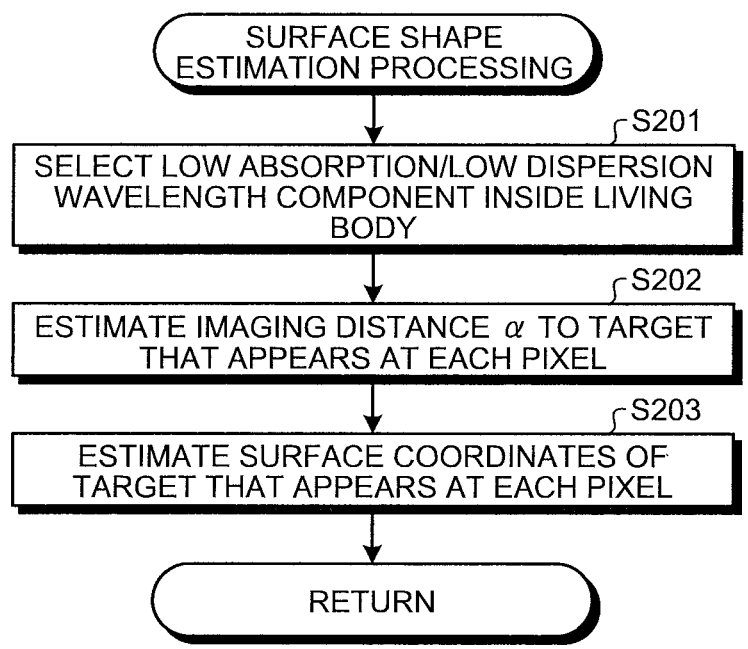
FIG. 4 is a flowchart illustrating an outline of surface shape estimation processing in FIG. 2.

FIG. 4 is a flowchart illustrating an outline of the surface shape estimation processing at Step S102 in FIG. 2.

As illustrated in FIG. 4, the low absorption wavelength component selection unit 201 selects a low absorption/low dispersion wavelength component inside a living body (Step S201). Specifically, an R component, for which the degree of absorption and dispersion inside a living body is the lowest, is selected. This is to obtain information on a pixel value that is correlated with an imaging distance to the best mucosal surface for which a reduction in the pixel value due to a blood vessel or the like that appears in the mucosal surface is prevented, to thereby improve the accuracy of imaging distance estimation to be performed in the subsequent stage.

Subsequently, the imaging distance estimation unit 20 estimates an imaging distance a to a target that appears at each of the pixels of the intraluminal image (Step S202). Specifically, the imaging distance is estimated in accordance with Equation (1) below using an assumed uniform diffuser based on the pixel value of the low absorption wavelength component.

$$\alpha(x_i, y_i) = \sqrt{\frac{I \times k \times \cos\theta}{L(x_i, y_i)}} \quad (1)$$

Here, $\alpha(x_i, y_i)$ represents an imaging distance to a target that appears at the coordinates $(x_i, y_i)$, I represents radiation intensity of a light source (measured in advance), K represents a diffuse reflection coefficient of a mucosal surface (an average value is measured in advance), θ represents an angle between a normal vector of the mucosal surface and a vector from the mucosal surface to the light source (which is a value determined based on a positional relationship between the light source at a distal end of the endoscope and the mucosal surface; in this example, an average value is set in advance), and $L(x_i, y_i)$ represents a pixel value of the low absorption wavelength component (R component) of the pixel at the coordinates $(x_i, y_i)$.

Figure 5:
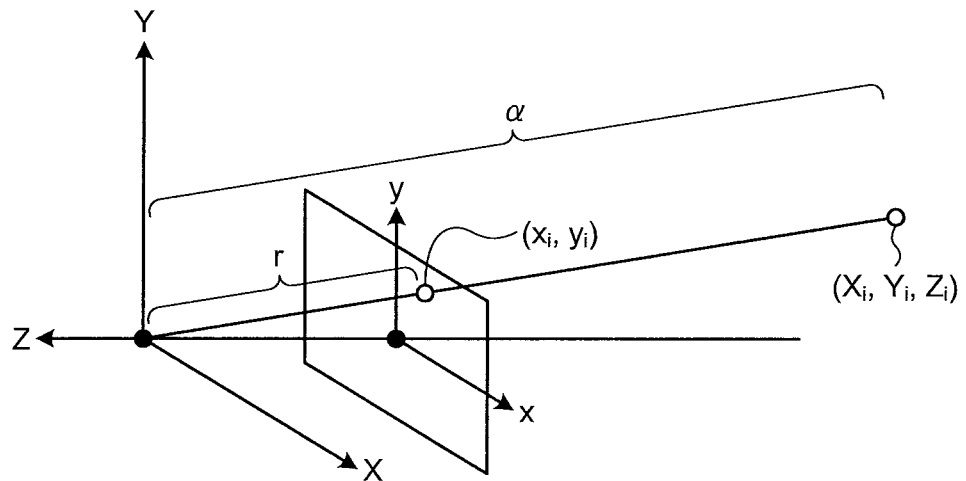
FIG. 5 is a schematic view for explaining a surface coordinates estimation method performed by an imaging distance estimation unit.

Thereafter, the surface shape estimation unit 10 estimates the surface coordinates of the target that appears at each of the pixels of the intraluminal image (Step S203). The coordinates $(x_i, y_i)$ in the image W1 (the origin is set at the center of the image) and surface coordinates $(X_i, Y_i, Z_i)$ of the target that appears at this coordinates have a relationship as illustrated in FIG. 5. Here, XYZ is a surface coordinate system with the XY axis parallel to the xy axis of the image W1 and the Z axis that passes through the center of the image. Further, f is a value that is determined based on a pixel pitch of a sensor, characteristics of an imaging system, or the like. α is the imaging distance estimated by the imaging distance estimation unit 20.

Equation (2) and Equation (3) below are obtained from the relationship illustrated in FIG. 5.

$$\frac{\alpha}{r} = \frac{X_i}{x_i} = \frac{Y_i}{y_i} = \frac{Z_i}{f} \quad (2)$$

$$r = \sqrt{x_i^2 + y_i^2 + f^2} \quad (3)$$

Accordingly, Equation (4) below is obtained from Equation (2) and Equation (3).

$$\begin{pmatrix} X_i \\ Y_i \\ Z_i \end{pmatrix} = \frac{\alpha}{\sqrt{x_i^2 + y_i^2 + f^2}} \begin{pmatrix} x_i \\ y_i \\ f \end{pmatrix} \quad (4)$$

In this manner, the surface shape estimation unit 10 performs conversion to the surface coordinate system based on the imaging distance to the target that appears at each of the pixels of the intraluminal image W1 and based on the coordinates of each of the pixels, and estimates the surface coordinates (surface shape) of the target (subject) that appears at each of the pixels. After Step S203, the image processing apparatus 1 returns to the main routine in FIG. 2.

Referring back to FIG. 2, processes from Step S103 will be described.

At Step S103, the imaging viewpoint changing unit 11 performs imaging viewpoint change processing for changing an imaging viewpoint with respect to the surface shape, e.g., for changing the imaging viewpoint from a first imaging viewpoint to a second imaging viewpoint.

Figure 6:
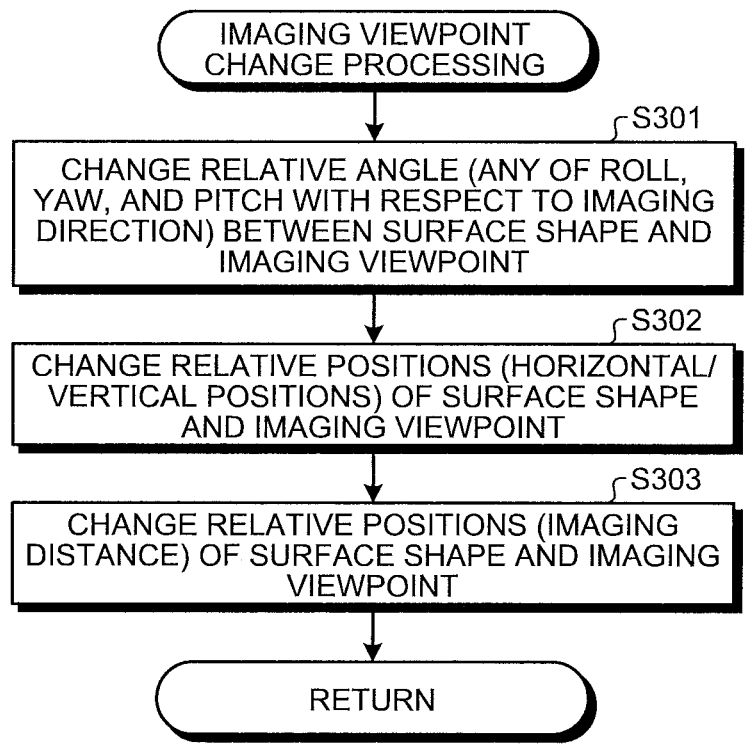
FIG. 6 is a flowchart illustrating an outline of imaging viewpoint change processing in FIG. 2.

FIG. 6 is a flowchart illustrating an outline of the imaging viewpoint change processing at Step S103 in FIG. 2.

Figure 7:
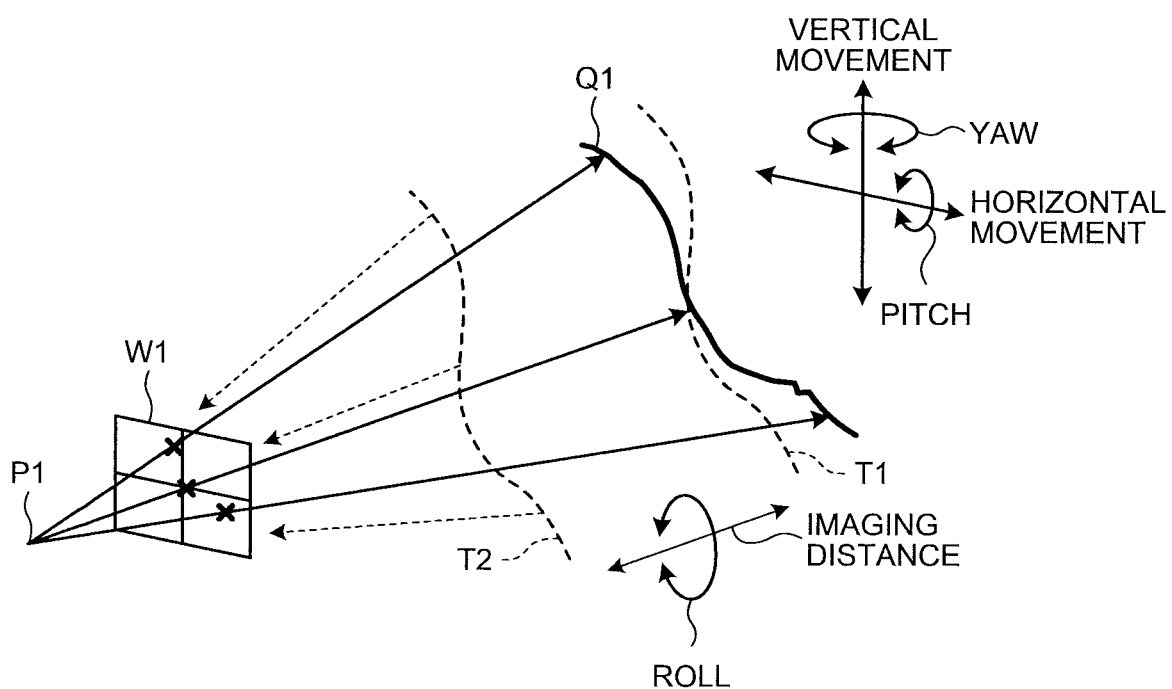
FIG. 7 is a schematic view for explaining a method of changing a relative angle by a relative angle changing unit.

As illustrated in FIG. 6, the relative angle changing unit 30 changes a relative angle between the surface shape and the imaging viewpoint (any of a roll angle, a yaw angle, and a pitch angle with respect to the imaging direction of the endoscope) (Step S301). Specifically, as illustrated in FIG. 7, a relative angle between a surface shape Q1 and an imaging viewpoint P1 is changed. More specifically, the rotation unit 300 performs conversion from the surface coordinate system XYZ to a barycentric coordinate system X0Y0Z0 with the origin at the center of mass of the surface shape, in accordance with Equation (5) below.

$$\begin{pmatrix} X0_i \\ Y0_i \\ Z0_i \end{pmatrix} = \begin{pmatrix} X_i \\ Y_i \\ Z_i \end{pmatrix} - \begin{pmatrix} X_c \\ Y_c \\ Z_c \end{pmatrix} \quad (5)$$

Here, $(X_c, Y_c, Z_c)$ represents barycentric coordinates of the surface shape.

Further, the rotation unit 300 changes a relative angle between the surface shape and the imaging viewpoint by X-axis rotation (pitch), Y-axis rotation (yaw), and Z-axis rotation (roll), in accordance with Equation (6) below. In FIG. 7, T1 indicates a surface shape that is obtained when the surface shape Q1 is changed as described above.

$$\begin{pmatrix} X0_i' \\ Y0_i' \\ Z0_i' \end{pmatrix} = \begin{pmatrix} \cos\theta_z & -\sin\theta_z & 0 \\ \sin\theta_z & \cos\theta_z & 0 \\ 0 & 0 & 1 \end{pmatrix} \quad (6)$$

$$\begin{pmatrix} \cos\theta_y & 0 & \sin\theta_y \\ 0 & 1 & 0 \\ -\sin\theta_y & 0 & \cos\theta_y \end{pmatrix} \begin{pmatrix} 1 & 0 & 0 \\ 0 & \cos\theta_x & -\sin\theta_x \\ 0 & \sin\theta_x & \cos\theta_x \end{pmatrix} \begin{pmatrix} X0_i \\ Y0_i \\ Z0_i \end{pmatrix}$$

Here, θx represents a rotation angle with respect to the X-axis, θy represents a rotation angle with respect to the Y-axis, and θz represents a rotation angle with respect to the Z-axis.

Subsequently, in the relative position changing unit 31, the horizontal/vertical position changing unit 311 changes relative positions (horizontal/vertical positions) of the surface shape and the imaging viewpoint (Step S302), and the imaging distance changing unit 312 changes an imaging distance from the surface shape to the imaging viewpoint (Step S303). Specifically, the horizontal/vertical position changing unit 311 changes the horizontal/vertical positions of the surface shape and the imaging viewpoint in accordance with Equation (7) below, and the imaging distance changing unit 312 changes the imaging distance from the surface shape to the imaging viewpoint in accordance with Equation (8). Then, conversion from the barycentric coordinate system X0Y0Z0 to the surface coordinate system XYZ is performed in accordance with Equation (9) below. In FIG. 7, T2 indicates a surface shape that is obtained when the surface shape T1 is changed as described above.

$$\begin{pmatrix} X0_i'' \\ Y0_i'' \end{pmatrix} = \begin{pmatrix} X0_i' \\ Y0_i' \end{pmatrix} + \begin{pmatrix} X_s \\ Y_s \end{pmatrix} \quad (7)$$

$$Z0_i'' = Z0_i' + Z_s \quad (8)$$

$$\begin{pmatrix} X_i'' \\ Y_i'' \\ Z_i'' \end{pmatrix} = \begin{pmatrix} X0_i'' \\ Y0_i'' \\ Z0_i'' \end{pmatrix} + \begin{pmatrix} X_c \\ Y_c \\ Z_c \end{pmatrix} \quad (9)$$

Here, $X_s$ represents an amount of change in the position in the X direction (horizontal direction), $Y_s$ represents an amount of change in the position in the Y direction (vertical direction), and $Z_s$ represents an amount of change in the position in the Z direction (amount of change in the imaging distance). After Step S303, the image processing apparatus 1 returns to the main routine in FIG. 2.

Referring back to FIG. 2, processes from Step S104 will be described.

At Step S104, the image generation unit 12 performs image generation processing of generating a virtual image of a target for a case of imaging the target from the changed imaging viewpoint.

Figure 8:
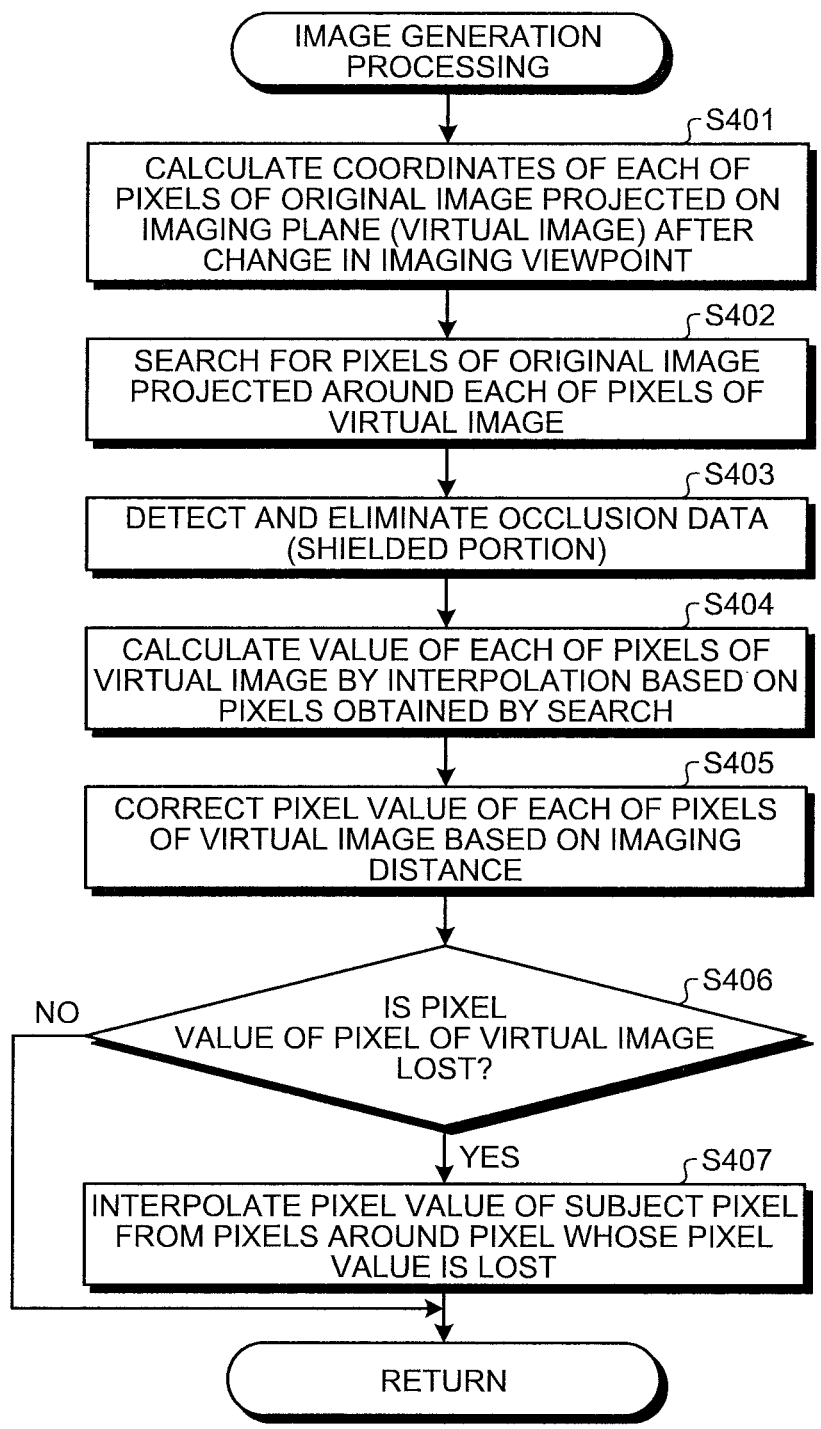
FIG. 8 is a flowchart illustrating an outline of image generation processing in FIG. 2.

FIG. 8 is a flowchart illustrating an outline of the image generation processing at Step S104 in FIG. 2.

As illustrated in FIG. 8, first, the pixel value estimation unit 40 calculates the coordinates of each of the pixels of the intraluminal image (original image) that is projected on an imaging plane after the change in the imaging viewpoint (Step S401). Specifically, coordinates $(x_i'', y_i'')$ of each of the pixels of the original image that is projected on the imaging plane (virtual image) after the change in the imaging viewpoint is calculated in accordance with Equation (10) below.

$$\begin{pmatrix} x_i'' \\ y_i'' \end{pmatrix} = \frac{f}{Z_i''} \begin{pmatrix} X_i'' \\ Y_i'' \end{pmatrix} \quad (10)$$

Subsequently, the search unit 401 searches for pixels of the original image that are projected around each of the pixels of the virtual image (Step S402). An integer coordinate in the xy coordinate system corresponds to the position of each of the pixels of the virtual image.

Thereafter, the shielded region elimination unit 403 detects and eliminates data (a pixel) corresponding to occlusion (shielded portion) in the virtual image from among the pixels of the original image projected on the virtual image (Step S403). Specifically, the shielded portion is determined and eliminated based on the imaging distances to the pixels of the original image projected around each of the pixels of the virtual image.

Subsequently, the pixel value interpolation unit 402 calculates a value of each of the pixels of the virtual image by performing interpolation based on the pixels obtained by search by the search unit 401 (Step S404).

Figure 9:
FIG. 9 is a diagram illustrating an example of a virtual image.
Figure 10:
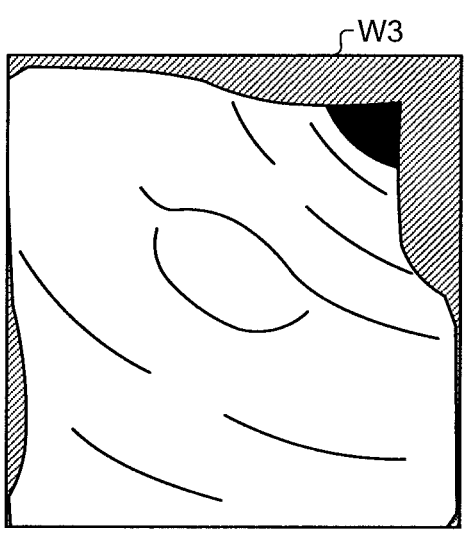
FIG. 10 is a diagram illustrating another example of a virtual image.

Thereafter, the distance-corresponding-pixel-value correction unit 404 corrects the pixel value of each of the pixels of the virtual image based on the imaging distance from the surface shape to the imaging viewpoint (Step S405). Specifically, the pixel value is corrected so as to be increased with a decrease in the imaging distance obtained after the change in the imaging viewpoint, and so as to be decreased with an increase in the imaging distance obtained after the change in the imaging viewpoint. Accordingly, it is possible to generate an image with the changed imaging viewpoint, such as a virtual image W2 illustrated in FIG. 9 and a virtual image W3 illustrated in FIG. 10.

Subsequently, if the pixel value of any of the pixels of the virtual image is lost (Yes at Step S406), the lost pixel value interpolation unit 41 interpolates the pixel value of the subject pixel from pixels around the pixel whose pixel value is lost (Step S407). After Step S406, the image processing apparatus 1 returns to the main routine in FIG. 2, and terminates the processing. In contrast, if the pixel value of any of the pixels of the virtual image is not lost (No at Step S406), the image processing apparatus 1 returns to the main routine in FIG. 2, and terminates the processing.

According to the first embodiment, when a virtual image is generated for a case of imaging a target that appears in the intraluminal image from an imaging viewpoint that is different from an actual imaging viewpoint, and even if image distortion due to the characteristics of the imaging system of the endoscope occurs, even if a pixel value varies due to a change in the imaging distance, or even if occlusion (shielded portion) occurs due to a surface shape of the target, it is possible to generate a virtual image (learning sample) that appropriately reflects the above-described states inside a lumen.

First Modification

Next, a first modification of the first embodiment will be described. In the first modification of the first embodiment, a surface shape estimation unit has a different configuration and performs different processing. In the following, a configuration of the surface shape estimation unit according to the first modification of the first embodiment will be first described, and thereafter, processing performed by the surface shape estimation unit according to the first modification of the first embodiment will be described. The same components as those of the image processing apparatus 1 of the first embodiment described above will be denoted by the same reference signs, and explanation thereof will be omitted.

Figure 11:
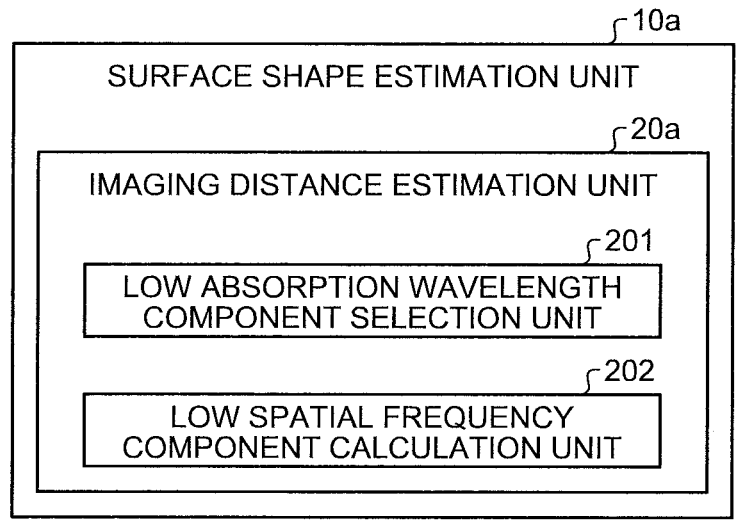
FIG. 11 is a block diagram illustrating a configuration of a surface shape estimation unit according to a first modification of the first embodiment.

FIG. 11 is a block diagram illustrating the configuration of the surface shape estimation unit according to the first modification of the first embodiment. A surface shape estimation unit 10a illustrated in FIG. 11 includes an imaging distance estimation unit 20a instead of the imaging distance estimation unit 20 of the first embodiment described above.

The imaging distance estimation unit 20a further includes a low spatial frequency component calculation unit 202 that calculates a low spatial frequency component for which a spatial frequency is low, in addition to the low absorption wavelength component selection unit 201.

Figure 12:
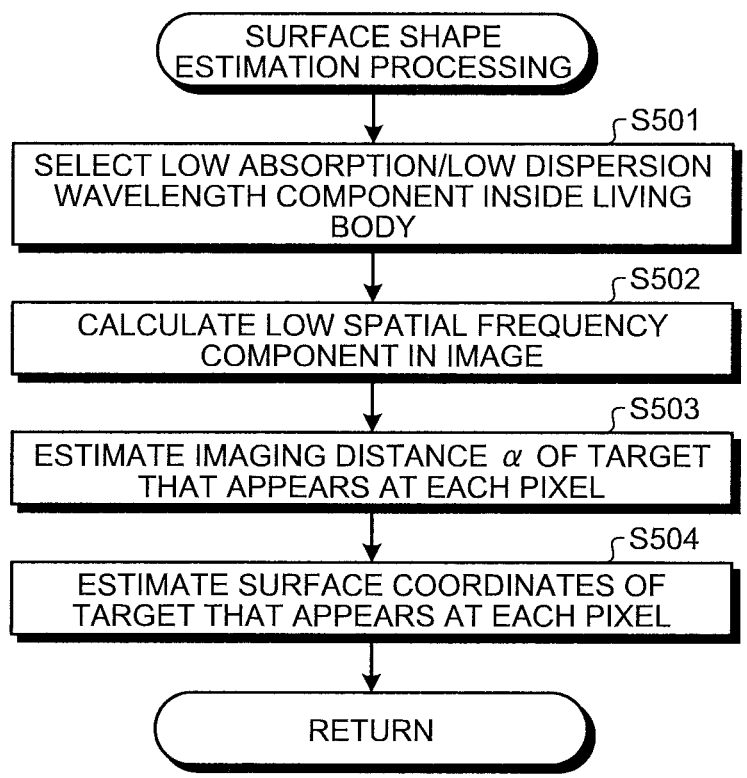
FIG. 12 is a flowchart illustrating an outline of surface shape estimation processing performed by the surface shape estimation unit according to the first modification of the first embodiment.

Next, surface shape estimation processing performed by the surface shape estimation unit 10a will be described. FIG. 12 is a flowchart illustrating an outline of the surface shape estimation processing performed by the surface shape estimation unit 10a. In the first modification of the first embodiment, processing other than the surface shape estimation processing performed by the surface shape estimation unit 10a is the same as the processing performed by the image processing apparatus 1 of the first embodiment described above (see FIG. 2), and therefore, explanation thereof will be omitted. Further, in FIG. 12, Step S501, Step S503, and Step S504 respectively correspond to Step S201, Step S202, and Step S203 in FIG. 4 described above, and therefore, explanation thereof will be omitted.

At Step S502, the low spatial frequency component calculation unit 202 calculates a low spatial frequency component for which a spatial frequency is low.

Specifically, a low spatial frequency component for which a spatial frequency is low is calculated using well-known smoothing processing or the like, and a noise component is eliminated. After Step S502, the image processing apparatus 1 proceeds to Step S503.

According to the first modification of the first embodiment as described above, it is possible to estimate a surface shape with reduced noise components, so that it is possible to generate a learning sample that appropriately reflects a state inside a lumen based on the estimated surface shape.

Second Modification

Next, a second modification of the first embodiment will be described. In the second modification of the first embodiment, an image generation unit has a different configuration and performs different processing. In the following, a configuration of the image generation unit according to the second modification of the first embodiment will be first described, and thereafter, processing performed by the image generation unit according to the second modification of the first embodiment will be described. The same components as those of the image processing apparatus 1 of the first embodiment described above will be denoted by the same reference signs, and explanation thereof will be omitted.

Figure 13:
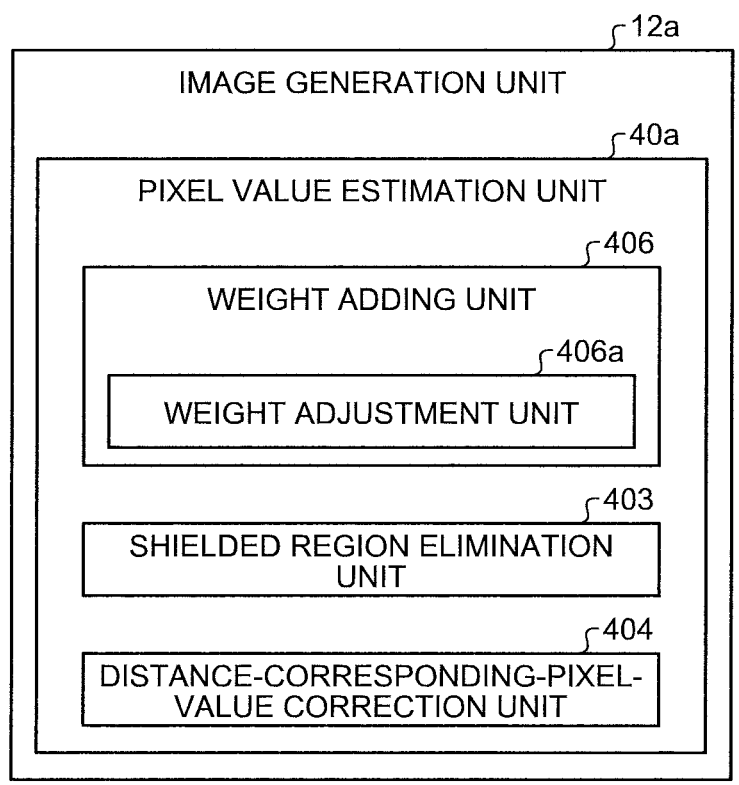
FIG. 13 is a block diagram illustrating a configuration of an image generation unit according to a second modification of the first embodiment.

FIG. 13 is a block diagram illustrating a configuration of the image generation unit according to the second modification of the first embodiment. An image generation unit 12a illustrated in FIG. 13 includes a pixel value estimation unit 40a instead of the pixel value estimation unit 40 of the first embodiment described above.

The pixel value estimation unit 40a includes a weight adding unit 406 that obtains a pixel value of each of the pixels of the virtual image by adding a weight, which corresponds to a distance between each of the pixels of the intraluminal image that is projected on the virtual image due to a change in the imaging viewpoint and each of the pixels of the virtual image, to the pixel value of each of the pixels of the intraluminal image, instead of the search unit 401 and the pixel value interpolation unit 402 of the first embodiment described above. Further, the weight adding unit 406 includes a weight adjustment unit 406a that adjusts the weight corresponding to the distance of each of the pixels of the virtual image, based on density information on the pixels of the intraluminal image projected on the virtual image.

Figure 14:
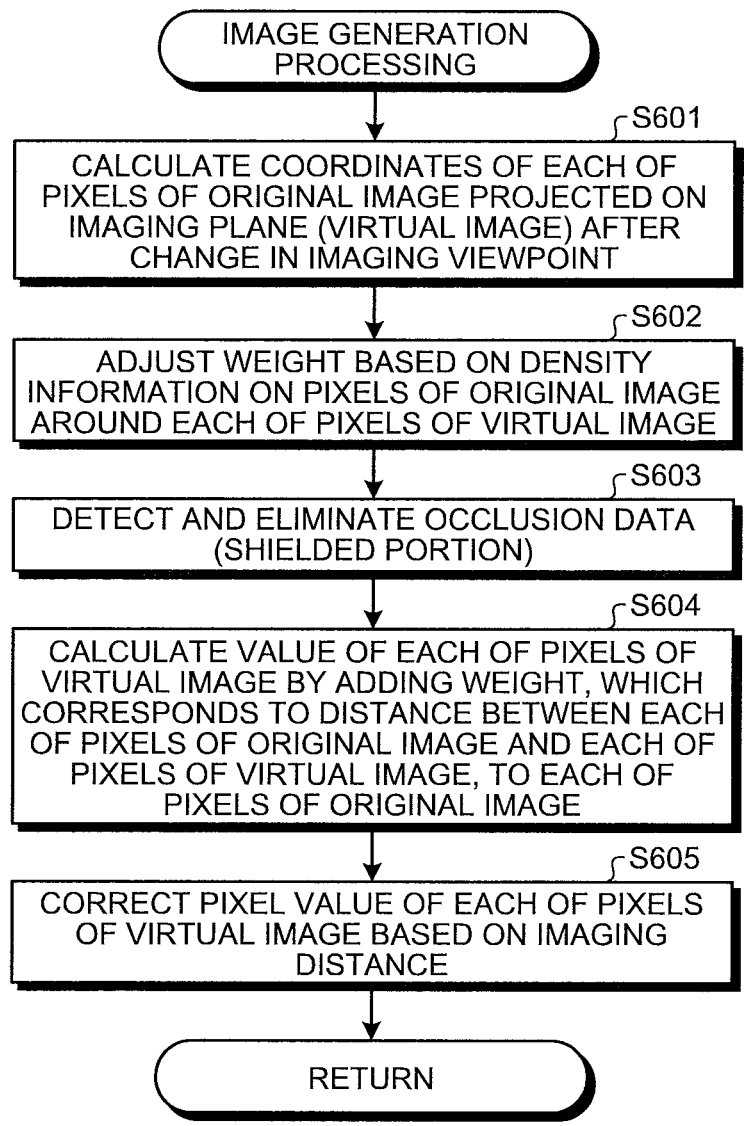
FIG. 14 is a flowchart illustrating an outline of image generation processing performed by the image generation unit according to the second modification of the first embodiment.

Next, image generation processing performed by the image generation unit 12a will be described. FIG. 14 is a flowchart illustrating an outline of the image generation processing performed by the image generation unit 12a. In the second modification of the first embodiment, processing other than the image generation processing performed by the image generation unit 12a is the same as the processing performed by the image processing apparatus 1 of the first embodiment described above (see FIG. 2), and therefore, explanation thereof will be omitted. Further, in FIG. 14, Step S601, Step S603, and Step S605 respectively correspond to Step S401, Step S403, and Step S405 in FIG. 8 described above.

At Step S602, the weight adjustment unit 406a adjusts the weight used by the weight adding unit 406 based on the density information on the pixels of the original image around each of the pixels of the virtual image. The weight is set in accordance with a distance between each of the pixels of the intraluminal image (original image) projected on the virtual image and each of the pixels of the virtual image. More specifically, the weight is set so as to be increased with a decrease in the distance and so as to be decreased with an increase in the distance by use of a Gaussian function or the like. The weight adjustment unit 406a adjusts the width of the Gaussian function, i.e., the degree of change in the weight according to the distance. More specifically, the weight is adjusted such that the width of the Gaussian function is increased when the density of pixels of the original image around a target pixel of the virtual image for which the pixel value is to be obtained through weighted addition is low, and the width of the Gaussian function is decreased when the density is high. After Step S602, the image processing apparatus 1 proceeds to Step S603.

At Step S604, the weight adding unit 406 calculates the value of each of the pixels of the virtual image by performing addition to each of the pixels of the original image based on the distance between each of the pixels of the original image projected on the virtual image and each of the pixels of the virtual image and based on the weight adjusted by the weight adjustment unit 406a. After Step S604, the image processing apparatus 1 proceeds to Step S605.

According to the second modification of the first embodiment as described above, it is possible to generate a learning sample that appropriately reflects a state inside a lumen.

Second Embodiment

Next, a second embodiment will be described. An image processing apparatus according to the second embodiment is different from the image processing apparatus 1 according to the first embodiment described above in that the imaging viewpoint changing unit 11 has a different configuration. In the following, a configuration of an imaging viewpoint changing unit according to the second embodiment will be described. The same components as those of the image processing apparatus 1 of the first embodiment described above will be denoted by the same reference signs, and explanation thereof will be omitted.

Figure 15:
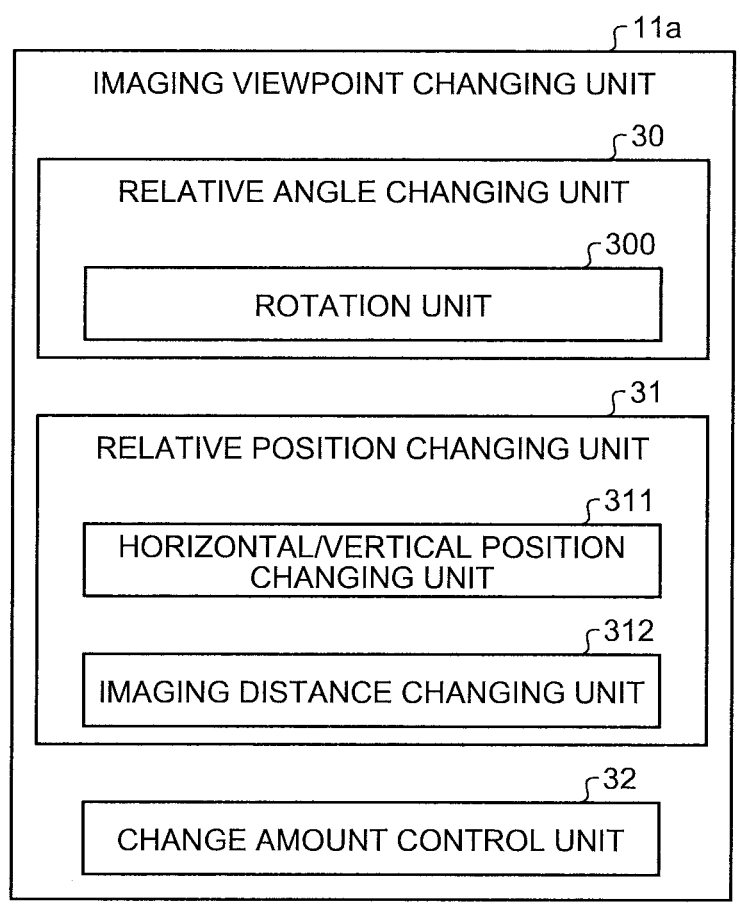
FIG. 15 is a block diagram illustrating a configuration of an imaging viewpoint changing unit according to a second embodiment.

FIG. 15 is a block diagram illustrating a configuration of the imaging viewpoint changing unit according to the second embodiment. An imaging viewpoint changing unit 11a illustrated in FIG. 15 further includes a change amount control unit 32, in addition to the components of the imaging viewpoint changing unit 11 of the first embodiment described above.

The change amount control unit 32 controls an amount of change in the imaging viewpoint such that data loss does not occur in the virtual image generated by the image generation unit 12 described above. Specifically, the same processing as the processing performed by the pixel value estimation unit 40 described above is performed to control an amount of change in the relative angle to be changed by the relative angle changing unit 30 and an amount of change to be performed by the relative position changing unit 31 such that the shielded portion (data lost portion) in the original image does not appear in the virtual image.

According to the second embodiment as described above, the change amount control unit 32 controls an amount of change in the imaging viewpoint such that data loss does not occur in the virtual image generated by the image generation unit 12. Therefore, it is possible to generate a learning sample that appropriately reflects a state inside a lumen.

Third Embodiment

Next, a third embodiment will be described. An image processing apparatus according to the third embodiment is different from the image processing apparatus 1 according to the first embodiment in that the arithmetic unit 7 has a different configuration. In the following, a configuration of an arithmetic unit according to the third embodiment will be described. The same components as those of the image processing apparatus 1 of the first embodiment described above will be denoted by the same reference signs, and explanation thereof will be omitted.

FIG. 16 is a block diagram illustrating a configuration of the arithmetic unit according to the third embodiment. An arithmetic unit 7c illustrated in FIG. 16 further includes an image generation frequency control unit 13, a learning unit 14, and a recognition unit 15, in addition to the components of the arithmetic unit 7 of the first embodiment described above.

The image generation frequency control unit 13 controls generation of a plurality of virtual images so as to increase the frequency of generation of a virtual image from an imaging viewpoint that tends to be used in actual imaging of an intraluminal image. Here, the imaging viewpoint that tends to be used in actual imaging of the intraluminal image is an imaging viewpoint at which a region from a mucosal surface that is located on the front side of a tract at a short imaging distance to a mucosal surface that is located in a deep part of the tract at a long imaging distance appears and at which a luminal wall appears in a lower part of the intraluminal image, for example. Specifically, the image generation frequency control unit 13 controls the imaging viewpoint changing unit 11 based on image information generated by the image generation unit 12, and increases the frequency of generation of a virtual image from the imaging viewpoint that tends to be used in actual imaging of the intraluminal image.

The learning unit 14 learns a parameter used for recognition of the intraluminal image based on the virtual image.

The recognition unit 15 recognizes an intraluminal image based on the parameter learned by the learning unit 14.

According to the third embodiment as described above, it is possible to generate a large number of learning samples from the imaging viewpoint that tends to be used in actual imaging of the intraluminal image. Therefore, it is possible to appropriately learn a parameter (for example, a recognition criterion for a color, a contour (edge), a pixel value surface shape (pixel value gradient), texture, or the like) of the recognition unit 15 using the learning sample that appropriately reflects the state. As a result, it is possible to improve the accuracy of the recognition unit 15 using the appropriately learned parameter.

OTHER EMBODIMENTS

The present disclosure may be realized by causing a computer system, such as a personal computer or a workstation, to execute an image processing program recorded in a recording apparatus. Further, the computer system may be used by being connected to other computer systems or other devices, such as servers, via a local area network (LAN), a wide area network (WAN), or a public line, such as the Internet. In this case, the image processing apparatus according to the first to third embodiments and the modifications may be configured to acquire image data of an intraluminal image via the above-described networks, output an image processing result to various output devices, such as a viewer or a printer, connected via the above-described networks, or store the image processing result in a storage device connected via the above-described networks, e.g., a recording medium that may be read by a reading device connected to the above-described networks, or the like.

The present disclosure is not limited to the first to third embodiments and the modifications. Variations may be made by appropriately combining a plurality of constituent elements disclosed in the embodiments and the modifications described above. For example, some constituent elements may be deleted from all of the constituent elements described in the embodiments and the modifications described above, or the constituent elements described in the embodiments and the modifications may be appropriately combined.

According to the present disclosure, it is possible to generate a learning sample that appropriately reflects a state inside a lumen.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor configured to:
estimate a first surface shape of a target that appears in an intraluminal image of a living body from a first viewpoint;
change an imaging viewpoint with respect to the first surface shape of the target that appears in the intraluminal image from the first viewpoint to a second viewpoint;
estimate, based on the first surface shape of the target estimated, a second surface shape of the target for a case of imaging the target from the second viewpoint;
generate a virtual image of the target for the case of imaging the target from the second viewpoint based on the second surface shape estimated; and
learn a parameter used for recognition of the target based on the virtual image.

2. The image processing apparatus according to claim 1, wherein the processor is configured to recognize the target based on the parameter.

3. The image processing apparatus according to claim 1, wherein the processor is configured to change the imaging viewpoint by changing positions of the first surface shape and the first viewpoint relative to each other.

4. The image processing apparatus according to claim 3, wherein the processor is configured to change the imaging viewpoint by changing horizontal positions and/or vertical positions of the first surface shape and the first viewpoint relative to each other.

5. The image processing apparatus according to claim 3, wherein the processor is configured to change the imaging viewpoint by changing an imaging distance from the first surface shape to the first viewpoint.

6. The image processing apparatus according to claim 1, wherein the processor is configured to change the imaging viewpoint by changing an angle between the first surface shape and the first viewpoint relative to each other.

7. The image processing apparatus according to claim 6, wherein the processor is configured to change the angle between the first surface shape and the first viewpoint relative to each other by rotating any one of roll, yaw, and pitch with respect to an imaging direction.

8. The image processing apparatus according to claim 1, wherein the processor is configured to control an amount of change in the imaging viewpoint such that data loss does not occur in the virtual image generated.

9. The image processing apparatus according to claim 1, wherein the processor is configured to estimate a pixel value of each of pixels of the virtual image based on pixel values of pixels of the intraluminal image that are projected on the virtual image due to a change in the imaging viewpoint.

10. The image processing apparatus according to claim 9, wherein the processor is configured to:
search for pixels of the intraluminal image that are projected around the each of the pixels of the virtual image due to a change in the imaging viewpoint; and
interpolate the pixel value of the each of the pixels of the virtual image based on pixel values of the pixels of the intraluminal image obtained by search.

11. The image processing apparatus according to claim 9, wherein the processor is configured to obtain a pixel value of each of the pixels of the virtual image by adding a weight, which corresponds to a distance between each of the pixels of the intraluminal image that is projected on the virtual image due to a change in the imaging viewpoint and each of the pixels of the virtual image, to the pixel value of each of the pixels of the intraluminal image.

12. The image processing apparatus according to claim 11, wherein the processor is to adjust a weight according to the distance based on density information on the pixels of the intraluminal image projected on the virtual image.

13. The image processing apparatus according to claim 9, wherein the processor is configured to eliminate a pixel corresponding to a shielded region in the virtual image among the pixels of the intraluminal image projected on the virtual image.

14. The image processing apparatus according to claim 9, wherein the processor is configured to correct a pixel value of each of the pixels of the virtual image based on an imaging distance from the first surface shape to the first viewpoint.

15. The image processing apparatus according to claim 9, wherein the processor is configured to, when a pixel value of a pixel of the virtual image cannot be estimated, interpolate the pixel value of the pixel of the virtual image for which the pixel value cannot be estimated from pixels around the pixel of the virtual image for which the pixel value cannot be estimated.

16. The image processing apparatus according to claim 1, wherein the processor is configured to control generation of a plurality of virtual images so as to increase frequency of generation of a virtual image from an imaging viewpoint to be used in actual imaging of an intraluminal image.

17. The image processing apparatus according to claim 1, wherein the processor is configured to estimate an imaging distance to the target that appears at each of pixels of the intraluminal image.

18. The image processing apparatus according to claim 17, wherein the processor is configured to:
select an absorption wavelength component of the pixels of the intraluminal image, for which a degree of absorption and dispersion inside a living body is below a predetermined value, in the intraluminal image; and
estimate the imaging distance to the target that appears at the each of the pixels of the intraluminal image based on the absorption wavelength component selected.

19. The image processing apparatus according to claim 17, wherein the processor is configured to:
calculate a spatial frequency component of the pixels of the intraluminal image, for which a spatial frequency is below a predetermined value, in the intraluminal image; and
estimate the imaging distance to the target that appears at the each of the pixels of the intraluminal image based on the spatial frequency component calculated.

20. An image processing method comprising:
estimating a first surface shape of a target that appears in an intraluminal image of a living body from a first viewpoint;
changing an imaging viewpoint with respect to the first surface shape of the target that appears in the intraluminal image from the first viewpoint to a second viewpoint;
estimating, based on the first surface shape of the target estimated, a second surface shape of the target for a case of imaging the target from the second viewpoint;
generating a virtual image of the target for the case of imaging the target from the second viewpoint based on the second surface shape estimated;
learning a parameter used for recognition of the target based on the virtual image.

21. A non-transitory computer-readable recording medium on which an executable program for an image processing apparatus is recorded, the program instructing a processor of the image processing apparatus to at least execute:
estimating a first surface shape of a target that appears in an intraluminal image of a living body from a first viewpoint;
changing an imaging viewpoint with respect to the first surface shape of the target that appears in the intraluminal image from the first viewpoint to a second viewpoint;
estimating, based on the first surface shape of the target estimated, a second surface shape of the target for a case of imaging the target from the second viewpoint;
generating a virtual image of the target for the case of imaging the target from the second viewpoint based on the second surface shape estimated; and learning a parameter used for recognition of the target based on the virtual image.

\* \* \* \* \*